United States Patent [19]
Montminy

[11] Patent Number: 5,814,459
[45] Date of Patent: Sep. 29, 1998

[54] PHOSPHOSPECIFIC TRANSCRIPTION FACTOR ANTIBODIES

[75] Inventor: Marc R. Montminy, Encinitas, Calif.

[73] Assignee: The Salk Institute for Biological Studies, San Diego, Calif.

[21] Appl. No.: 442,181

[22] Filed: May 15, 1995

Related U.S. Application Data

[63] Continuation of Ser. No. 16,839, Feb. 12, 1993, abandoned.

[51] Int. Cl.$^6$ .......................... G01N 33/53; G01N 33/536; C07K 16/18; C07K 7/04
[52] U.S. Cl. .......................... 435/7.1; 424/9.1; 424/193.1; 424/139.1; 424/195.11; 424/152.1; 424/172.1; 424/185.11; 435/7.2; 435/7.21; 436/536; 436/804; 530/327; 530/388.2; 530/358; 530/388.9; 530/389.2; 530/387.9; 530/391.1; 530/391.3; 530/402; 530/403
[58] Field of Search .......................... 424/193.1, 195.11, 424/185.11, 9.1, 139.1, 152.1, 172.1; 435/7.1, 7.2, 7.21; 530/327, 388.2, 358, 388.9, 389.2, 391.1, 391.3, 402, 403, 387.9; 536/23.1, 23.5; 514/14

[56] References Cited

U.S. PATENT DOCUMENTS 5,599,681  2/1997  Epstein et al. .......................... 435/7.23

OTHER PUBLICATIONS

Levine et al., J. Immunol. Methods, 124:239–250, 1989 Abstract thereof.

Hagiwara et al., Molec Cell Biol, vol. 13, 4852–59, 1993.

Waldmann, Science, vol. 252, 1657–62, 1991.

Gonzalez, Cell, vol. 59, 675–80, 1989.

Rudinger, Chapter 1, from "Peptide Hormones" Ed. J.A. Parsons, University Park Press, 1976.

Goding, Chapters 3 and 8, from "Monoclonal Antibodies: Principles and Practices," Academic Press, 1986.

Meinkosh et al., Molec Cell Biol., vol. 11, 1759–64, 1991.

Harris et al., TIBTECH, vol. 11, 42–44, 1993.

Struthers et al., Nature, vol. 350, 622–624, 1991.

Gonzalez et al., Nature, vol. 337, 749–752, 1989.

Ginty, et al., Regulation of CREB Phosphorylation in the Suprachiasmatic Nucleus by Light and a Circadian Clock; *Science*, 260:238–241, 1993.

*Primary Examiner*—Ronald B. Schwadron
*Attorney, Agent, or Firm*—Fish & Richardson P.C.

[57]  ABSTRACT

Phospho-specific antibodies which recognize the phosphorylated forms of cAMP-responsive transcription factors are provided.

14 Claims, 4 Drawing Sheets

PHOSPHOSPECIFIC TRANSCRIPTION FACTOR ANTIBODIES

This is a continuation of application Ser. No. 08/016,839, filed Feb. 12, 1993, now abandoned.

BACKGROUND OF THE INVENTION

1. Field of the Invention

The present invention relates generally to the regulation of gene expression and specifically to phosphorylated transcription factors which bind to a cyclic-AMP response element of a gene resulting in activation of the gene and to phospho-specific antibodies which inhibit the transcription factor mediated gene activation.

2. Description of Related Art

Transcriptional regulation of gene expression is an important component of the cellular changes mediated by second messenger signal transduction pathways in response to extracellular stimuli. In eukaryotes the most common mechanism by which the second messenger cyclic-AMP (cAMP) amplifies extracellular signals is by stimulating the activity of the cAMP-dependent protein kinase A (PKA).

In mammals, the best characterized transcriptional response to cAMP is mediated by the transcription factor CREB (cAMP Response Element Binding factor) and its family members. PKA activates CREB by phosphorylating a single serine at position 133 (ser133) through a mechanism that apparently does not change CREB's affinity for its DNA binding site in the gene promoter, the cAMP Response Element, CRE. The CRE sequence, typically TGACGTCA, is also recognized by other members of the CRE-binding transcription factor family including the Activating Transcription Factor (ATF) subfamily, CRE-Binding Protein-1 (CRE-BP1), cAMP-Responsive Element Modulator (CREM) and others. The ATF-subfamily is involved in regulating many cellular and viral genes whose promoters contain CREs and are responsive to other stimuli, including the adenovirus transactivator E1A protein. All members of the CREB/ATF family have on their C-terminus a conserved leucine zipper dimerization domain juxtaposed to a DNA-binding domain rich in basic amino acids.

The CREB subfamily is distinguished from the ATF subfamily by a conserved phosphorylation/activation region (kinase inducible domain, or KID), that contains consensus phosphorylation sites for a variety of protein kinases, including PKA, protein kinase C, casein kinase I and II and others. The PKA phosphoacceptor serine (Ser133) in CREB is necessary for CREB activation in response to cAMP. Negatively charged amino acids cannot substitute for the phosphoacceptor serine. The modulation of CREB activity in vivo could occur by several possible mechanisms, including the extent of CREB phosphorylation/dephosphorylation or alternate site phosphorylation.

A number of neurotransmitters and neuroactive drugs regulate target neurons through the cAMP second messenger pathway. Although cAMP may in turn stimulate transcription of specific cellular genes, the conditions under which such transcriptional controls are employed in the brain remain uncharacterized. The psychomotor stimulant cocaine, for example, augments cAMP production by inhibiting the dopamine reuptake transporter, suggesting that this drug might correspondingly activate the cAMP responsive transcription factor CREB.

A growing number of transcription factors appear to be regulated by phosphorylation, therefore phospho-specific antibodies for these factors would be invaluable for examining transcriptional regulation in the brain. These antibodies would also be important for modulating genes whose expression is dependent on phosphorylated transcription factor activation. The present invention provides such phospho-specific antibodies.

SUMMARY OF THE INVENTION

The present invention provides antibodies which bind to the phosphorylated form of cAMP-responsive transcription factors. The antibodies of the invention find particular utility as reagents for detecting the presence of the phosphorylated form of transcription factors as compared with unphosphorylated forms in such tissues as neurological tissue.

DETAILED DESCRIPTION OF THE INVENTION

The present invention provides antibodies which are specifically immunoreactive with phosphorylated forms of a cAMP-responsive transcription factors, wherein the antibodies are reactive with polypeptide fragments consisting essentially of about 11 to about 17 amino acid residues, wherein about 5 to about 8 amino acid residues are positioned on each side of the serine phosphorylation site. The invention also provides a method for detecting a phosphorylated transcription factor and a method of inhibiting activation of a gene by phosphorylated transcription factor. Also included in the invention is a method of identifying a composition which modulates phosphorylation of a transcription factor in neuronal tissue. The invention also provides an isolated polypeptide consisting essentially of the amino acid residues from about 128 to about 141 of the CREB protein and conservative variations thereof and the phosphorylated form of the peptide.

The term "antibody" as used herein, refers to immunoglobulin molecules and immunologically active portions of immunoglobulin molecules, i.e., molecules that contain an antigen binding site or paratope. Examples of such antibody molecules are intact immunoglobulin molecules, substantially intact immunoglobulin molecules and those portions of an immunoglobulin molecule that contain the paratope, including those portions known in the art as Fab, Fab', F(ab')$_2$ and F(v).

The antibody of the invention may be a polyclonal or monoclonal antibody, for example. Antibodies provided by the present invention are immunoreactive with the phosphorylated form of transcription factor. Antibody which consists essentially of numerous monoclonal antibodies with different epitopic specificities (polyclonal antibodies), as well as distinct monoclonal antibody preparations are provided.

An antibody composition useful in the present invention is an anti-peptide antibody characterized as containing antibody molecules that specifically immunoreact with a phosphorylated form of a cAMP-responsive transcription factor. The transcription factor may be for example, CREB, ATF-1 or CREM. By "specifically immunoreacts", is meant that the antibody binds to the phosphorylated form of transcription factor and does not bind to the unphosphorylated form of the same transcription factor. Therefore, the antibodies of the invention can distinguish between the phosphorylated (i.e., active form) and unphosphorylated form of a transcription factor. Preferably, the antibody should immunoreact with an epitopic site of a phosphorylated transcription factor in such a way that it is capable of inhibiting transcription factor mediated gene activation as well.

As used in this invention, the term "epitopic site" refers to an antigenic determinant that consists of chemically active surface groupings of molecules such as amino acids or sugar side chains and usually have specific three dimensional structural characteristics, as well as specific charge characteristics. The preferred epitopic site of the invention is a peptide fragment consisting essentially of about 11 to about 17 amino acid residues, wherein about 5 to about 8 amino acid residues are positioned on each side of the serine phosphorylation site.

In general, the purified epitopic peptides have a cysteine attached at the C-terminus to permit unidirectional attachment of the synthetic peptide to an immunogenic protein through a connecting bridge, for example, maleimidobenzoylated (MB)-keyhole limpet hemocyanin (KLH). Other immunogenic conjugates can also be used, for example, albumin, and the like. The resulting structure may have several peptide structures linked to one molecule of protein. The invention also provides an immunogenic composition comprising the polypeptide of the invention conjugated to a carrier protein, as described above.

The host subject is immunized by administering the antigen, usually in the form of a protein conjugate, as indicated above, by any suitable method, preferably by injection, either intraperitoneally, intravenously, subcutaneously, or by intra-foot pad. Adjuvants may be included in the immunization protocol.

The initial immunization with the protein bound antigen can be followed by several booster injections given periodically at intervals of several weeks. The antibody contained in the plasma of each host can then be tested for its reactivity with the immunizing polypeptide of the invention. The host having the highest response is usually most desirable as the donor of the antibody secreting somatic cells used in the production of hybridomas. Alternatively, hyperimmunization can be effected by repeatedly injecting additional amounts of peptide-protein conjugate by intravenous and/or intraperitoneal route.

Antibody compositions useful in the present invention can be produced using various production systems well known in the art, such as by initiation of monoclonal hybridoma culture comprising a hybridoma that secretes antibody molecules of the appropriate polypeptide specificity. The culture is maintained under conditions and for a period of time sufficient for the hybridoma to secrete the antibody molecules into the medium. The antibody containing culture medium is then collected and antibody molecules can be further isolated by well known techniques. Monoclonal antibodies useful according to the method of the invention can also be purified from ascites fluid or recombinantly cloned (Huse, et al., *Science,* 246:1275, 1989; Mullinax, et al., *Proc. Natl. Acad. Sci. USA,* 87:8095, 1990; Sastry, et al., *Proc. Natl. Acad. Sci., USA,* 86:3833, 1989).

Numerous techniques can be utilized to produce a monoclonal antibody which specifically immunoreacts with the polypeptide of the invention without resorting to undue experimentation. To a great extent, the production of such monoclonal antibodies is rendered routine because of the highly defined nature of the polypeptide of the invention. Thus, whether the polypeptide of the invention is used for immunization and/or screening, the very limited number of immunogenic determinants on the polypeptide greatly simplifies the identification of cell lines producing monoclonal antibodies of the invention, for example, by limiting the repertoire of clonal expression possible.

One very useful type of cell line for expression of the monoclonal antibodies of the invention is the hybridoma. The general method used for production of hybridomas producing monoclonal antibodies is well known (Kohler, et al., *Nature* 256:495, 1975; *Current Protocols in Molecular Biology*, Ausubel, et al., ed., 1989). The resulting hybridomas are then screened for production of monoclonal antibodies capable of binding to the polypeptide of the invention.

Methods for generating hybridomas producing (secreting) antibody molecules having a desired immunospecificity, i.e., having the ability to immunoreact with a particular protein and/or polypeptide, are well known in the art. Particularly applicable is the hybridoma technology described by Niman et al. (*Proc. Natl. Acad. Sci. USA,* 80:4949, 1983). The techniques of sensitization and/or immunization, cell fusion, ascites production, selection of mixed hybridomas, or subcloning of monoclonal hybridomas are generally well known in the art. Attention is directed to Koprowski, et al., U.S. Pat. No. 4,172,124, Koprowski, et al., U.S. Pat. No. 4,196,265, or Douillard, J. Y. and Hoffman, T., *Basic Facts about Hybridomas, in Compendium of Immunology,* Vol. II, L. Schwartz, ed. (1981), which are herein incorporated by reference.

The isolation of hybridomas producing monoclonal antibodies that immunoreact with the polypeptide of the invention can be accomplished using routine screening techniques which permit determination of the elementary reaction pattern of the monoclonal antibody of interest. Thus, if a monoclonal antibody being tested binds with the phosphorylated transcription factor polypeptide and can block activation of a gene typically activated by phosphorylated transcription factor, then the antibody being tested and the antibody produced by a preferred hybridomas of the invention are equivalent.

Alternatively, since the invention teaches polypeptides or amino acid sequences which are specifically required for binding of a preferred monoclonal antibody of the invention, it is now possible to use these peptides for purposes of immunization to produce hybridomas which, in turn, produce monoclonal antibodies specific for the polypeptide. This approach has the added advantage of decreasing the repertoire of monoclonal antibodies generated by limiting the number of antigenic determinants presented at immunization by the polypeptide. The monoclonal antibodies produced by this method can be screened for specificity using standard techniques, for example, by binding polypeptide to a microtiter plate and measuring binding of the monoclonal antibody by an ELISA assay.

It is also possible to determine, without undue experimentation, if a monoclonal antibody has the same specificity as a preferred antibody of the invention by ascertaining whether the former prevents the latter from binding the polypeptide of the invention. If the monoclonal antibody being tested competes with the antibody of the invention, as shown by a decrease in binding by the antibody of the invention, then it is likely that the two antibodies bind to the same, or a closely related epitope.

Still another way to determine whether a monoclonal antibody has the specificity of a preferred monoclonal antibody of the invention is to pre-incubate the monoclonal antibody being tested with the polypeptide of the invention and then add a preferred antibody known to bind the polypeptide to determine if the preferred antibody is inhibited in its ability to bind the antigen. If the preferred antibody is inhibited then, in all likelihood, the monoclonal antibody being tested has the same, or a closely related, epitopic specificity as a preferred monoclonal antibody of the invention.

Under certain circumstances, monoclonal antibodies of one isotype might be more preferable than those of another in terms of their diagnostic or therapeutic efficacy. Particular isotypes of a monoclonal antibody can be prepared either directly, by selecting from the initial fusion, or prepared secondarily, from a parental hybridoma secreting a monoclonal antibody of different isotype by using the sib selection technique to isolate class-switch variants (Steplewski, et al., *Proc. Natl. Acad. Sci., U.S.A.,* 82:8653, 1985; Spira, et al., *J. Immunol. Methods,* 74:307, 1984). Thus, the preferred monoclonal antibodies of the invention would include class-switch variants having specificity for a phosphorylated transcription factor polypeptide of the invention.

Another embodiment of the present invention provides a method for detecting the presence of phosphorylated transcription factors in vitro and in vivo, comprising contacting a phospho-specific antibody of the invention with a sample suspected of containing phosphorylated transcription factor and measuring the reactivity of the antibody and the phosphorylated transcription factor. Although the sample may be any tissue or various body fluids from a subject, preferably the sample is neurological tissue.

The phospho-specific antibody of the invention is suited for in vitro use, for example in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Those of skill in the art will know of or can readily discern, other immunoassay formats without undue experimentation.

The antibodies of the invention can be bound to many different carriers and used to detect the presence of phosphorylated transcription factor. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, bioluminescent compounds, colloidal metals, and chemiluminescent compounds. Those of ordinary skill in the art will know of other suitable labels for binding to the monoclonal antibodies of the invention, or will be able to ascertain such, using routine experimentation. Furthermore, the binding of these labels to the antibodies of the invention can be done using standard techniques common to those of ordinary skill in the art.

The antibodies of the invention can be used for in vivo detection of phosphorylated transcription factor. The detectably labeled monoclonal antibody is given in a dose which is diagnostically effective. The term "diagnostically effective" means that the amount of detectably labeled antibody is administered in sufficient quantity to enable detection of the site having the phosphorylated transcription factor for which the antibodies are specific.

The concentration of detectabley labeled antibody which is administerd should be sufficient such that the binding of phosphorylated transcription factor is detectable compared to background. Further, it is desireable that the detectably labeled antibody be rapidly cleared from the circulatory system in order to give the best target to background signal ratio.

For in vivo diagnostic imaging, the type of detection instrument available is a major factor in selecting a given radioisotope. The radioisotope chosen must have a type of decay which is detectable for a given type of instrument. Still another factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethlenediaminetetraacetic acid EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Ar, and $^{201}$Tl.

The antibody of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The phospho-specific antibodies of the invention are useful as screening tools for identifying compositions which modulate phosphorylation of a transcription factor, for example in neuronal tissue. Thus, in another embodiment, the invention provides a method for identifying a composition which affects a transcription factor in neuronal tissue comprising contacting the neuronal tissue with the composition, under conditions sufficient to allow the components to interact, then subsequently detecting the interaction between phosphorylated neuronal transcription factor and phospho-specific antibody of the invention. The observed effect of the composition on the phosphorylation of the transcription factor is either inhibitory or stimulatory. For example, a neuroactive composition may exhibit either an antagonistic or agonist effect, thereby inhibiting or stimulating phosphorylation of transcription factor in the neuronal tissue, can be identified using the method of the invention.

The present invention also provides polypeptides comprising at least 14 amino acids which contain an epitopic site consisting essentially of the amino acid residues from about 128 to about 141 of the CREB protein, and conservative variations thereof. Also provided are corresponding polypeptides which are phosphorylated at the serine at position 133. The invention provides antibodies reactive with the phosphorylated peptide and a method for detecting the presence of phosphorylated CREB in a cell. Alternatively, phospho-specific antibodies can be used to detect the presence of other phosphorylated cAMP-responsive transcription factors.

A preferred embodiment of the invention comprises the epitopic polypeptide LSRRPSYRKILNDL (SEQ ID NO:1), and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. As long as the polypeptide is able to compete with native phosphorylated transcription factor for binding to an antibody with the specificity of the preferred antibody of the invention, it is included in the invention.

When a polypeptide of the present invention has a sequence that is not identical to the sequence of native phosphorylated transcription factor because one or more conservative or non-conservative substitutions have been made, usually no more than about 20 percent of the amino acid residues are substituted.

The peptides of the invention can be synthesized by such well known solid phase synthesis methods described by Merrifield (J. Am. Chem. Soc. 85:21–49, 1962) and Stewart and Young (Solid Phase Peptides Synthesis (Freeman, San Francisco, 1969, pp.27–62), using copoly(styrene-divinylbenzene) containing 0.1–1.0 mMol amines/g polymer. On completion of chemical synthesis, the peptides can be deprotected and cleaved from the polymer by treatment with liquid HF-10% anisole for about ¼–1 hours at 0° C. After evaporation of the reagents, the peptides are extracted from the polymer with 1% acetic acid solution which is then lyophilized to yield the crude material. This can normally be purified by such techniques as gel filtration on SEPHADEX G-15 an ion exchange resin using 5% acetic acid as a solvent. Lyophilization of appropriate fractions of the column will yield the homogeneous peptide or peptide derivatives, which can then be characterized by such standard techniques as amino acid analysis, thin layer chromotography, high performance liquid chromatography, ultraviolet absorption spectroscopy, molar rotation, solubility, and quantitated by the solid phase Edman degradation.

During or after the synthesis, reactive amino acids are protected by various blocking groups, for example, cysteines may be blocked by 3,4-dimethylbenzyl (DMB) groups, arginines and histidines by tosyl(TOS) groups, aspartic acid and glutamic acids by benzyl (BZL) groups, and lysines by 2-chlorobenzyloxyl-carboxyl (2-CBZ) groups. Other protective blocking groups are well known, and can be used in the present invention. Those of ordinary skill in the art will know of other techniques for peptide synthesis, or can readily ascertain such techniques, without resorting to undue experimentation.

Alternatively, the polypeptides of the invention can be produced using recombinant techniques commonly known to those of skill in the art (see, for example, Current Protocols in Molecular Biology, Ausubel, et al., eds., Wiley Interscience Press, 1989, incorporated herein by reference).

A preferred embodiment comprises CREB polypeptide phosphorylated at a serine at position 133 (ser133). In vivo, cAMP stimulates CREB activity via the protein kinase A mediated phosphorylation of ser133. The invention provides antibodies which are specific for the phosphorylated peptide, for example, phospho-CREB. Phospho-CREB antiserum may be polyclonal or monoclonal as described above. Antibodies which consist essentially of pooled monoclonal antibodies with different epitopic specificities, as well as distinct monoclonal antibody preparations are provided.

The invention also provides an isolated polynucleotide sequence encoding the CREB peptide which contains the amino acid residues from about 128 to about 141 of the CREB protein. As used herein, "polynucleotide sequence" refers to a polymer of deoxyribonucleotides or ribonucleotides, in the form of a separate fragment or as a component of a larger construct. DNA encoding the CREB polypeptide containing the phosphorylation site can be assembled from cDNA fragments or from oligonucleotides which provide a synthetic DNA sequence which is capable of being expressed in a recombinant transcriptional unit. Polynucleotide sequences of the invention include DNA, RNA and cDNA sequences.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the formation of cDNA sequences. Among the standard procedures for isolating cDNA sequences of interest is the formation of cDNA libraries (plasmid or phage), which are derived form reverse transcription of mRNA which is abundant in donor cells that have a high level of genetic expression. When used in combination with polymerase chain reaction (PCR) technology, even rare expression products can be cloned. In those cases where significant portions of the amino acid sequence of the polypeptide are known, the production of labeled single or double-stranded DNA or RNA probe sequences duplicating a sequence putatively present in the target CDNA may be employed in DNA/DNA hybridization procedures which are carried out on cloned copies of the cDNA which have been denatured into a single-stranded form (Jay, et al., *Nucleic Acid Research*, 11:2325, 1983).

The polynucleotide sequence encoding the CREB phosphorylation site can be synthesized by the PCR technique with the appropriate primers and a nucleotide sequence encoding CREB. The polynucleotide sequence of the invention includes the deduced nucleotide sequence encoding the amino acid sequence, LSRRPSYRKILNDL (SEQ ID. NO:1), and conservative variations thereof.

In yet another embodiment, the invention provides a method of inhibiting gene activation by phosphorylated transcription factor utilizing a phospho-specific antibody of the invention. The antibody is useful for inhibiting the activation of cAMP responsive genes. For example, such cAMP-inducible genes whose activity is modulated by CREB include the proto-oncogene c-fos and the somatostatin gene. Therefore, addition of phospho-specific antibody which binds CREB will interfere with induction of the c-fos or somatostatin gene. Induction of c-fos by cAMP has been linked to proliferative states associated with Graves disease (thyroid tumor) and acromegally (pituitary tumor).

The following examples are intended to illustrate but not limit the invention. While they are typical of those that might be used, other procedures known to those skilled in the art may alternatively be used.

EXAMPLE 1

PRODUCTION OF PHOSPHO CREB-SPECIFIC ANTIBODY

Figure 1:
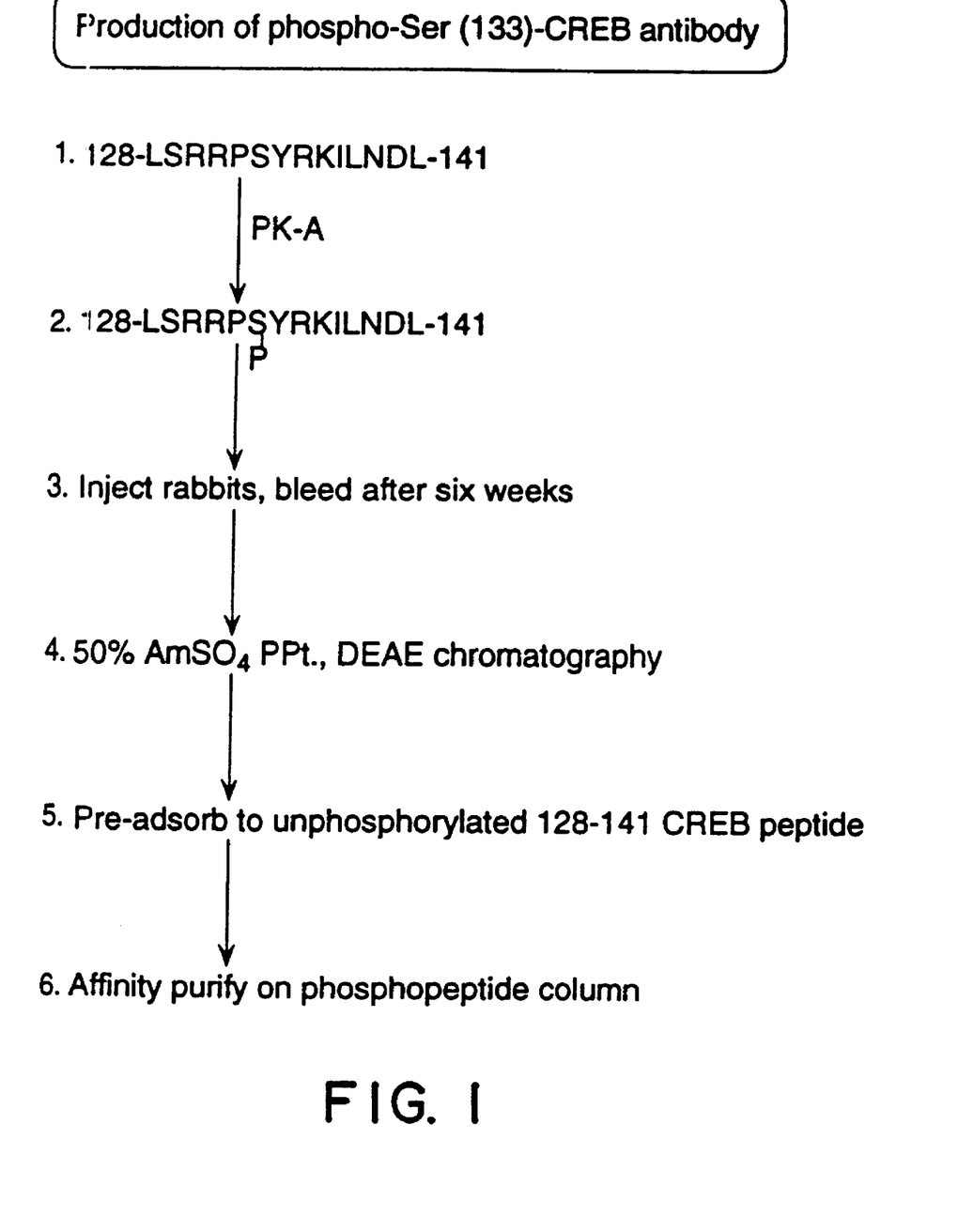
FIG. 1 is a schematic illustration of the phospho-specific antibody purification.

A synthetic CREB peptide extending from residues 128–141 and containing the PK-A phosphorylation site at Ser 133 was prepared to produce phospho-Ser133 CREB specific antiserum. The sequence of CREB peptide (in single letter code) and the corresponding amino acid number within the CREB protein are shown in FIG. 1). A CREB peptide containing residues 128–141 was synthesized using the standard t-Boc method and then purified by reverse-phase HPLC. The purified peptide was coupled to keyhole limpet hemocyanin (KLH) according to the method described by Vaughan et al., (*Methods in Enzymology*, 168:588, 1989), and phosphorylated by incubation with 10 $\mu$g/ml of C-subunit of kinase A, 1 mM ATP, 2 mM MgCl$_2$, 2 mM Tris-HCl (pH 7.0) at 30° C. for 3 hrs. The coupled phosphopeptide (100 $\mu$g) was emulsified in Freund's complete adjuvant and injected subcutaneously into rabbits on a biweekly schedule. Rabbits were bled 6 weeks after initial injection. IgG was precipitated from serum by 50% saturated ammonium sulfate, and partially purified by DEAE-CELLULOSE ion exchange resin chromatography to remove protein phosphatases in serum. A majority of the CREB (128–141) phosphopeptide was dephosphorylated upon injection, therefore the non-discriminating CREB antibodies were removed by adsorption on unphosphorylated CREB peptide resin. The antibody against unphosphorylated CREB was adsorbed using unphosphorylated peptide coupled to an affigel 10 resin. Phospho-CREB specific antibody, named 5322, was further purified by affinity chromatography with phosphopeptide resin. Eluate fractions containing phospho-specific antiserum 5322 were further purified by phospho (128–141) peptide chromatography. FIG. 1 is a schematic illustration of the phospho-specific antibody purification.

Figure 2A:
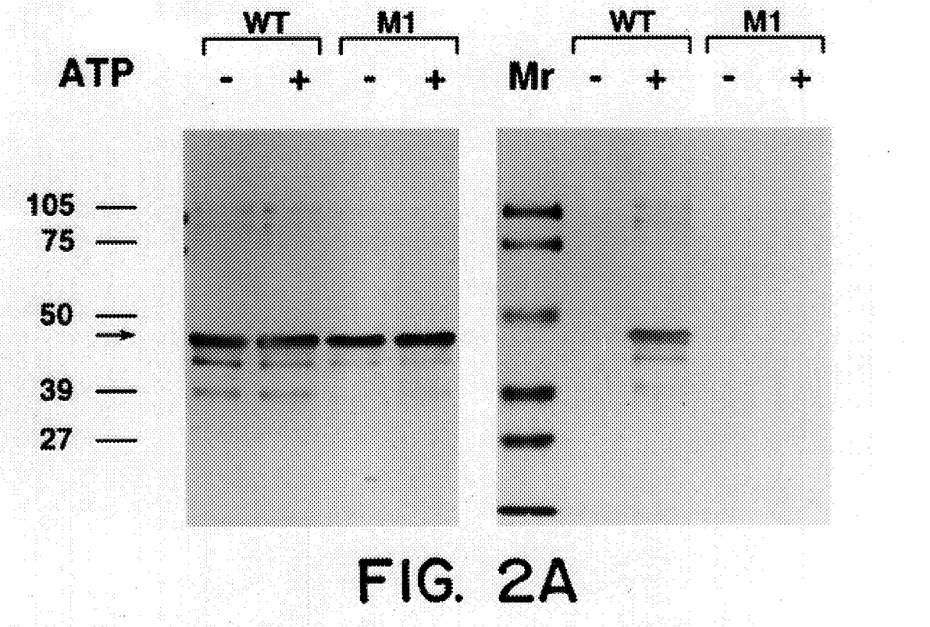
FIG. 2A shows an immunoblot of recombinant CREB (WT) and CREB-M1 (M1) proteins.

Immunoblot analysis revealed that the affinity purified antiserum 5322 could discriminate between dephospho and PK-A phosphorylated CREB protein whereas CREB antiserum 220 (Gonzalez, et al., *Nature* 337:749, 1989), raised against a synthetic CREB peptide, from amino acids 136–150, could not. FIG. 2A shows an immunoblot of recombinant CREB (WT) and CREB-M1 (M1) proteins. CREBM1 contains Ser133 to Ala133 substitution, which destroys the PK-A phosphorylation site. (−) and (+) indicate absence or presence of ATP in reactions containing CREB (or M1) protein plus the catalytic subunit of PK-A. The left panel shows a Western blot using CREB antibody 220 (220-Ab) raised against a synthetic peptide spanning residues 136–150. The right panel shows an immunoblot with purified 5322 antibody. The arrow points to the 43 kD CREB band. Smaller protein bands are digestion products of CREB and CREB-M1. Bacterial CREB and CREB-M1 proteins were incubated with C-subunit of PK-A in the presence or absence of ATP. After 30 min incubation at 30° C., samples (0.5 $\mu$g each) were then resolved by SDS-PAGE and transferred to a nitrocellulose membrane. Antiserum 5322 was unable to recognize PK-A treated CREB-M1 protein which contains a Ser133 to Ala133 substitution, suggesting that phosphorylation of Ser133 was critical for immunoreactivity.

Figure 2B:
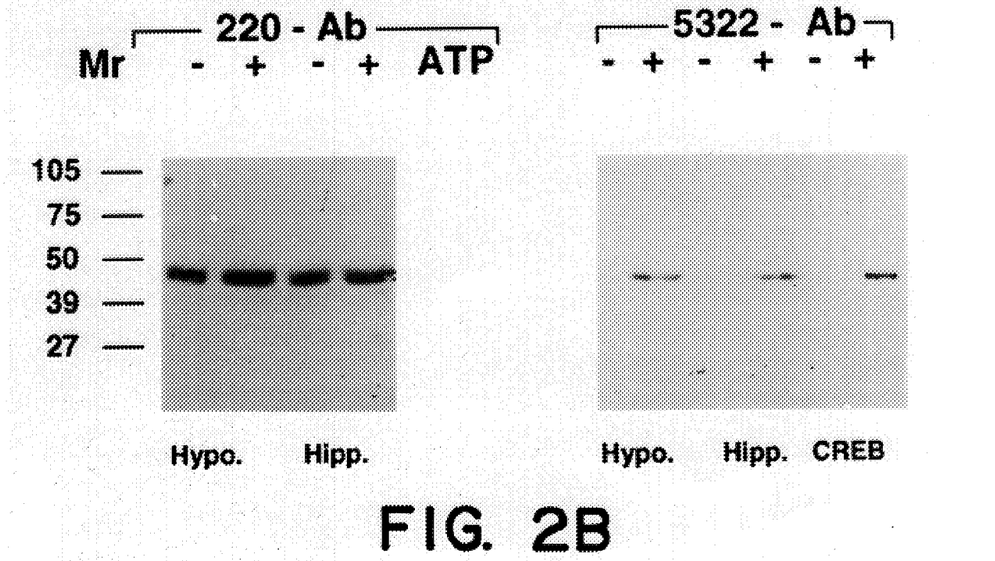
FIG. 2B shows an immunoblot analysis of phospho-CREB in rat brain tissues.

To determine the extent to which antiserum 5322 was selective for phosphorylated CREB protein versus other cellular substrates of PK-A, crude extracts of rat brain, including hippocampus, and hypothalamus were analyzed by Western blot. FIG. 2B shows an immunoblot analysis of phospho-CREB in rat brain tissues. Nuclear extracts (10 $\mu$g protein) prepared from rat hypothalamus (Hypo.) and hippocampus (Hipp.) were incubated with C-subunit of kinase A (0.1 $\mu$g) in the presence (+) or absence (−) of 100 $\mu$M ATP and resolved by SDS-PAGE. The left panel shows the immunoblot with antibody 220, showing apparently the same amount of CREB in each samples. The right panel shows the immunnoblot with 5322 antibody, recognizing only phospho-CREB in the brain. Recombinant CREB protein (CREB) is shown as a positive control. The 5322 antiserum distinguished a single 43 kD CREB band following in vitro phosphorylation with PK-A but not in untreated samples. By contrast, the non-discriminating 244 CREB antiserum showed no change in levels of the 43 kD CREB immunoreactive band. Surprisingly, other CREB related genes like ATF-1 (39 kD) and CREM (21 kD) expression did not cross-react with this antiserum, thereby allowing specific assessment of CREB activity in these tissues.

EXAMPLE 2

CREB PHOSPHORYLATION AND SOMATOSTATIN EXPRESSION IN PC12 CELLS

Figure 3A:
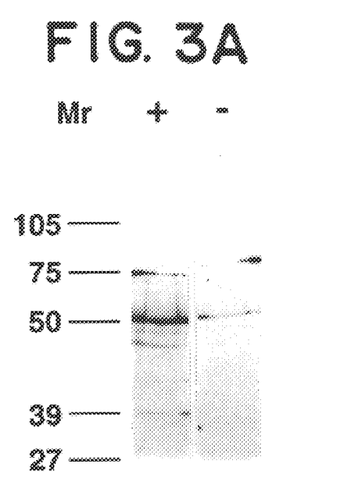
FIG. 3A shows an immunoblot analysis of nuclear extracts prepared from control (−) and forskolin-treated (+) PC12 cells using phospho-specific 5322 antiserum. (Mr, relative mass (in kD) as indicated).
Figure 3B:
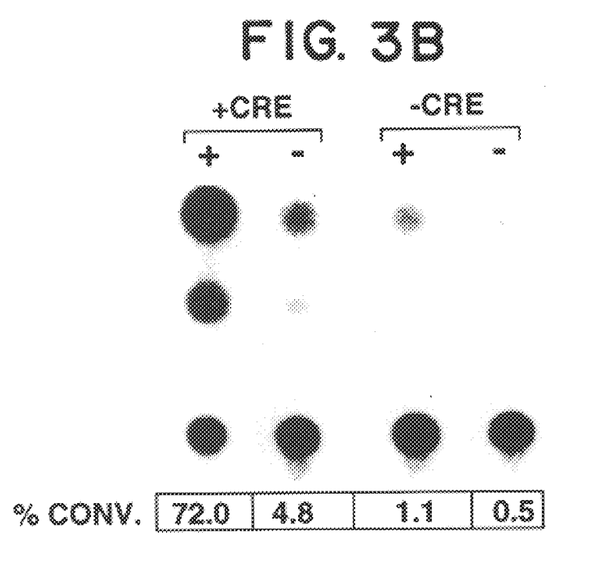
FIG. 3B shows a transient CAT assay of PC 2 cells using wild-type (+CRE) or mutant (−CRE) somatostatin-CAT reporter genes.

CREB immunoreactivity prior to and following treatment of PC12 pheochromocytoma cells with forskolin was compared to test whether the 5322 antiserum could detect CREB phosphorylation after induction by cAMP in living cells. FIG. 3A shows an immunoblot analysis of nuclear extracts prepared from control (−) and forskolin-treated (+) PC12 cells using phospho-specific 5322 antiserum. (Mr, relative mass (in kD) as indicated). A single 43 kD immunoreactive CREB band was specifically enhanced within 30 minutes of treatment and was accompanied by a 15 to 20-fold induction in the activity of the cAMP responsive somatostatin gene. FIG. 3B shows a transient CAT assay of PC12 cells using wild-type (+CRE) or mutant (−CRE) somatostatin-CAT reporter genes. Following transfection with CAT reporter plus RSV-βgal plasmid as internal control, cells were either treated with 10 $\mu$M forskolin (+) or ethanol vehicle (−) (%

CONV, percent conversion of $^{14}$C-chloramphenicol to acetylated forms). The increase in phospho-CREB immunoreactivity correlated well with the peak phosphorylation of Ser 133 as determined previously by 2-D tryptic mapping studies. The increased phosphorylation of CREB detected here does not arise from de novo synthesis of the protein since no change in CREB immunoreactivity with forskolin treatment was detectable with the non-discriminating CREB 220 antiserum.

EXAMPLE 3

Figure 4:
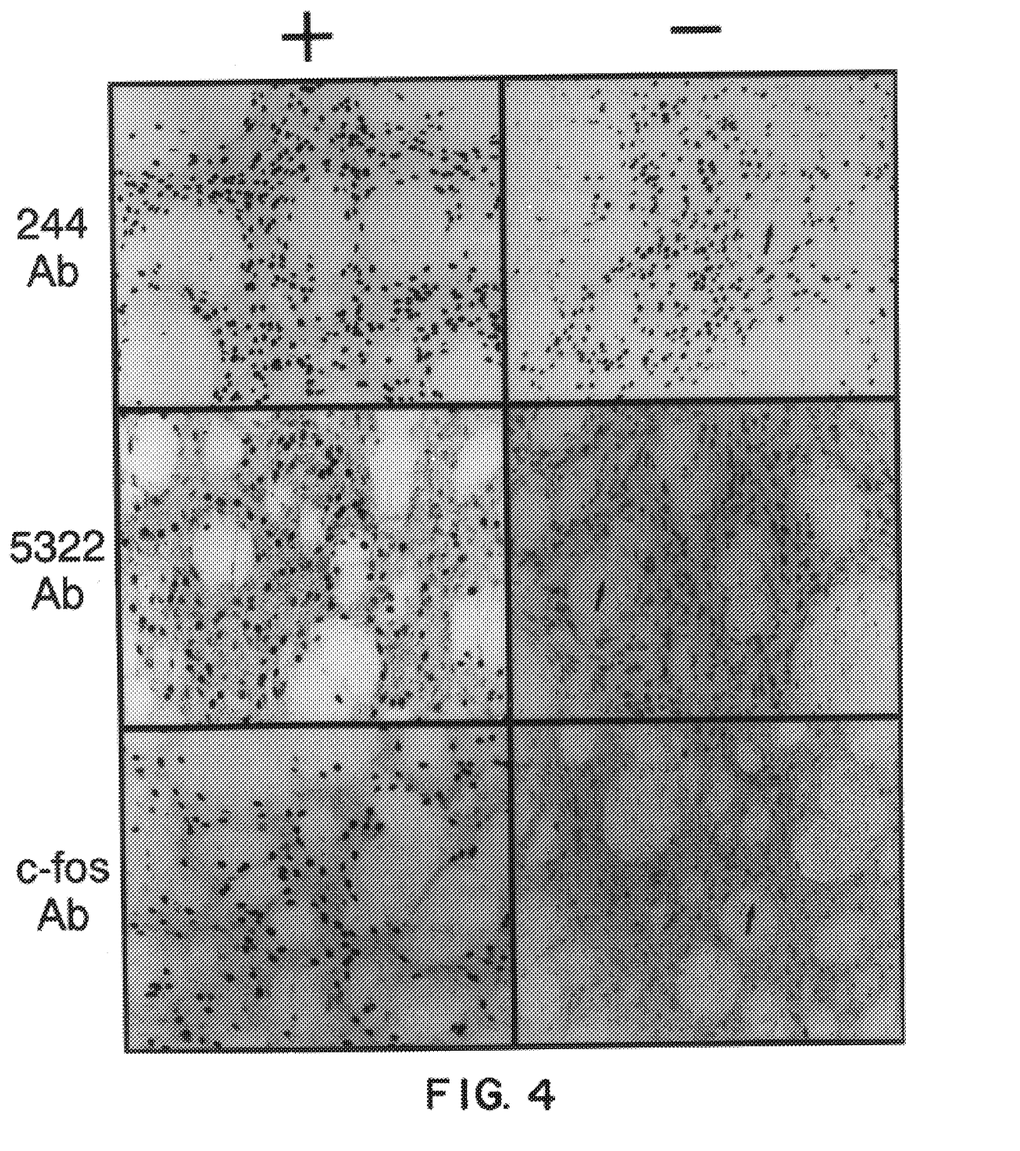
FIG. 4 shows unreactive myelinated corticofugal fiber bundles coursing through the caudate-putamen (arrows). The upper panel shows immunostaining from sections incubated with non-discriminating (phospho and dephospho CREB) CREB Antibody 244. The middle panel shows sections treated with phosphoSer133-specific antibody 5322. The lower panel denotes c-fos expression as detected by polyclonal c-fos antibody. (Photomicrograph magnification 20×).

EFFECTS OF COCAINE OR SALINE ON CREB PHOSPHORYLATION AND c-fos EXPRESSION IN NEURONS Previous studies have shown that striatal neurons in the basal ganglia could be stimulated by dopamine D1-receptor agonists (Shof, et al., *Nature*, 2:366, 1981). These studies examined the corresponding stimulation of CAMP to observe the relationship between CREB phosphorylation and activation of transcription of CAMP responsive genes. Cocaine has been shown to activate these neurons by inhibiting the reuptake transporter, thereby increasing synaptic levels of dopamine. Cocaine was examined to see whether CREB activity could be synaptically regulated. Sprague-Dawley male albino rats (250 g) were used for all experiments. All rats were housed in groups for at least 5 days prior to testing under a 12:12 light/dark cycle and standard ambient temperature. Food and water were available ad libitum. Animals were intravenously cannulated and injected with cocaine or vehicle on an hourly schedule over a 3 hour treatment period. Thirty minutes after treatment, rats (N=3 per group) were deeply anaesthetized and perfused transcardially with heparinized saline followed by cold 4% paraformaldehyde in 0.1M NaPO$_4$ buffer. Tissue sections were prepared and stained for CREB or c-fos as described previously (Torres, et al., *Brain Res.* 571:204, 1992). Stained sections were then treated with the chromogen DAB, washed with KPBS, mounted onto gelatin chrome alum-coated slides, and counterstained with pyronon Y. Representative coronal brain sections (40 μm) were counterstained with pyronon Y from male rats injected with cocaine hydrochloride (+) (5 mg/kg;iv) or saline vehicle (−) (0.9% NaCl). In FIG. 4 the arrows point to unreactive myelinated corticofugal fiber fundles coursing through the caudate-putamen. The upper panel shows immunostaining from sections incubated with non-discriminating (phospho and dephospho CREB) CREB Antibody 244. The middle panel shows sections treated with phosphoSer133-specific antibody 5322. The lower panel denotes c-fos expression as detected by polyclonal c-fos antibody. (Photomicrograph magnification 20×). Sham-injected animals showed only modest numbers of phospho-CREB immunoreactive cells distributed randomly throughout the caudate-putamen (FIG. 4). Acute injection of cocaine, however, evoked a dramatic increase in the number and intensity of phospho-CREB immunoreactive cells within the striatum. Moreover, this immunoreactivity was specifically blocked when the 5322 antiserum was preincubated with the CREB 128–141 phosphopeptide but not the unphosphorylated peptide.

By contrast with the increase in phospho-CREB immunoreactive cells noted within the striatum, no consistent changes were observed in other regions of the brain including the hippocampus, hypothalamus, and cortex. Within the striatum, the induction in CREB phosphorylation was accompanied by a comparable increase in c-fos immunoreactivity (FIG. 4b) as previously described (Graybiel, et al., *Proc. Natl. Acad. Sci., USA*, 87:6912, 1990). These results are consistent with previous findings from ours and other laboratories indicating the CREB binds to and activates the c-fos gene in response to cAMP (Dwarki, et al., *EMBO. J.* 9:225, 1990).

The foregoing is meant to illustrate, but not to limit, the scope of the invention. Indeed, those of ordinary skill in the art can readily envision and produce further embodiments, based on the teachings herein, without undue experimentation.

---

---

I claim:

1. An antibody which binds to phosphorylated CREB polypeptide fragment consisting of the amino acid sequence set forth in SEQUENCE ID NO. 1, wherein the polypeptide fragment is phosphorylated at serine at position 6, but does not bind to ATF-1, CREM, or non-phosphorylated CREB.

2. The antibody of claim 1, wherein the antibody is polyclonal.

3. The antibody of claim 1, wherein the antibody is monoclonal.

4. A method for detecting phosphorylated CREB transcription factor, comprising contacting an antibody according to claim 1 with a permeabilized cell sample or cell lysate suspected of containing phosphorylated transcription factor and measuring the reactivity of antibody and transcription factor.

5. The method of claim 4, wherein the sample is neurological tissue.

6. The method of claim 4, wherein the antibody is detectably labeled.

7. The method of claim 6, wherein the label is selected from the group consisting of radioisotope, fluorescent compound, a bioluminescent compound and chemiluminescent compound.

8. The method of claim 4, wherein the contacting is done in vitro.

9. A method of identifying a composition which modulates phosphorylation of a transcription factor in neural tissue, which comprises:

a. contacting the neural tissue with the composition; and b. detecting the interaction between phosphorylated neuronal transcription factor and the antibody of claim 1.

10. The method of claim 9, wherein the composition is an agonist.

11. The method of claim 9, wherein the composition is an antagonist.

12. An isolated polypeptide consisting of the amino acid sequence recited in SEQUENCE ID NO. 1.

13. The polypeptide of claim 12, having the sequence LSRRPSYRKILNDL, wherein the serine residue at position 6 is phosphorylated.

14. An immunogenic compound comprising the polypeptide of claim 13 conjugated to a carrier protein, with the proviso that the carrier protein is not an intact CREB molecule.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear     ( i i ) MOLECULE TYPE: peptide     ( i x ) FEATURE:
        ( A ) NAME/KEY: Peptide
        ( B ) LOCATION: 1..14

( x i ) SEQUENCE DESCRIPTION: SEQ ID NO:1:

Leu Ser Arg Arg Pro Ser Tyr Arg Lys Ile Leu Asn Asp Leu
    1                   5                       10